United States Patent [19]

Zhong et al.

[11] Patent Number: 5,281,529
[45] Date of Patent: Jan. 25, 1994

[54] METHOD FOR IN VITRO SEXUAL REPRODUCTION OF CORN PLANTS

[75] Inventors: Heng Zhong, East Lansing; Masomeh B. Sticklen, Okemos, both of Mich.

[73] Assignee: Board of Trustees operating Michigan State University, East Lansing, Mich.

[21] Appl. No.: 977,117

[22] Filed: Nov. 16, 1992

[51] Int. Cl.$^5$ .............................................. A01H 4/00
[52] U.S. Cl. .......................... 435/240.45; 435/240.5; 435/172.3; 47/58
[58] Field of Search ............. 435/240.4, 240.49, 240.5, 435/240.45, 172.3; 47/58.03

[56] References Cited

PUBLICATIONS

Bajaj (May 1979) Indian Journal of Experimental Biology 17:475–478.
Polowick, et al (1984) Can. J. Botany 62:830–834.
Irish, et al. (1991) Development 112:891–898.
Krishnamoorthy, et al. (1976) Z. Pflanzenphysiol. Bd. 79S:91–94.
Bommineni, et al (1987) Amer. J. Botany 74(6):883 ∝ 890.
Rhodes, et al (1986) Plant Science 46:225–232.
Polowick, P. L. and Greyson, R. I., Can J. Bot. 63 2196–2199 (1985).
Sladky, Z., Havel, L., Biol. Plant 18 469–472 (1976).
Gengenbach, B. G., Planta 134 91–93 (1977).
McDaniel, C. N., Poethig, R. S., Planta 175 13–22 (1988).
Irish, E. E., and Nelson, T., Plant Cell 1 737–744 (1989).
Murashige, T., and Skoog, F., Physiol Plant. 15 473–497 (1962).
Polowick, P. L. Greyson, R. I., Plant Sci. Lett. 26 139–145 (1982).
Sheridan, W. F., Annu. Rev. Genet. 22 353–385 (1988).
Pareddy, D. R., Petolino, J. F., Plant Sci. 67 211–219 (1990).

*Primary Examiner*—Che S. Chereskin
*Attorney, Agent, or Firm*—Ian C. McLeod

[57] ABSTRACT

A method for in vitro sexual reproduction in corn plants is described. The method involves differentiation of shoot tips with N$^6$-benzyladenine (BA) into ears and then ovaries and pollinating the ovaries to produce kernels. The kernels are then germinated to produce the plant. The method is particularly useful for maintaining lives of corn and for genetic manipulation by using different pollens.

9 Claims, 7 Drawing Sheets

METHOD FOR IN VITRO SEXUAL REPRODUCTION OF CORN PLANTS

BACKGROUND OF THE INVENTION

(1) Field of the Invention

The present invention relates to a method for in vitro sexual reproduction of corn plants. It is disclosed that the complete developmental sequence of corn from seedling shoot tips to ears with normal ovaries and kernels with viable embryos (i.e. seed to seed) can be achieved using a single set of in vitro experimental conditions. Clusters of ears can also be regenerated from in vitro cultured axillary buds of corn.

(2) Prior Art

There are reports where each stage of corn development was individually achieved in vitro. Corn plants were grown from isolated shoot meristems and flowered in the greenhouse (Irish, E. E., Nelson T. M., Development 112 891-898 (1991). Young tassels (staminate) and ears (pistillate) of corn were also grown to maturity in cultures (Bommeneni, V. R., Greyson, R. I., Am. J. Bot. 74 883-890 (1987); Polowick, P. L. and Greyson, R. I., Can. J. Bot. 63 2196-2199 (1985)). in vitro fertilization of ovaries (Sladky, Z., Havel, L., Biol. Plant. 18 469-472 (1976); Dhaliwal, S., King, P., Theor. Appl. Genet., 13 43-48 (1978)) and development of normal kernels (caryopses) with embryos have also been reported Gengenbach, B. G., Planta 134 91-93 (1977) What is needed is a method which allows the whole sequence of development of corn in vitro.

Corn shoot meristem is temporally and spatially programmed to form various organs (see e.g. McDaniel, C. N., Poethig, R. S., Planta 175 13-22 (1988)). The physiological basic of tassel and ear development in corn is not clear, although the developmental morphology of flower formation has been extensively studied for many years (Irish, E. E., and Nelson, T., Plant Cell 1 737-744 (1989)). Corn inflorescences are first hermaphrodite and later become staminate (tassel) or pistillate (ear) inflorescences by selective suppression of pistils in the terminal tassel and stamens in the axillary ear. Sex expression in plants appears to be controlled by the endogenous growth regulators. Regardless of the photoperiodic requirement, gibberellins synthesized in leaves favor male flower formation while the root-produced cytokinins enhance female flower production. Gibberellin (GA) has been indirectly implicated to female flower development in corn based on the exogenous application and by assay of gibberellins in tassel or ear mutants of corn. Exogenous application of GA did feminize potential tassels (Krishnamoorthy, H. N., and Talukdar, A. R., Z. Pflanzenphysiol. 79 91-94 (1976)). However, unequivocal proof of direct involvement of gibberellins in ear development is lacking (Irish, E. E., and Nelson, T., Plant Cell 1 737-744 (1989)).

There is a need for a method for the in vitro production of different varieties of corn plant which is relatively simple and reliable.

OBJECTS

It is therefore an object of the present invention to provide a method for the production of corn plants from an in vitro sequence of steps beginning with the shoot tips (meristem) of a corn plant. Further, it is an object of the present invention to provide a method which allows corn plants to be produced by an in vitro fertilization method. Further still, it is an object of the present invention to provide a method wherein different varieties of corn can be produced by an in vitro method. These and other objects will become increasingly apparent by reference to the following description and the drawings.

IN THE DRAWINGS

FIG. 1 is a chart showing the pattern of shoot clump formation and somatic embryogenesis from shoot pieces and immature inflorescences of corn, At., medium for immature tassel culture; Ae., medium for immature ear culture. The medium composition was as follows:

At.   MS+500 mg/L   CH+4.5$\mu$M BA+0.45$\mu$M2,4-D

Ae. MS+500 mg/L CH+9.0$\mu$M BA

MS+500 mg/L CH+4.5$\mu$M 2,4-D

C. MS+500 mg/L CH+9.0$\mu$M2,4-D

D. MS+500 mg/L CH+4.5$\mu$M BA+2.25$\mu$M 2,4-D

E. MS+2.25$\mu$M BA+1.8$\mu$M IBA

F. MS+3.6$\mu$M IBA

FIG. 2 is a chart showing the morphogenetic pathways of shoot, tassel and ear differentiation in shoot-tip and immature inflorescence cultures of corn. The medium composition was as follows:

A.   MS+500 mg/L   CH+4.5$\mu$M BA+0.45$\mu$M2.4-D

B. MS+500 mg/L CH+9.0$\mu$M BA

C. MS+500 mg/L CH+1.0$\mu$M BA

D. MS+1.0$\mu$M BA+1.8$\mu$M IBA or MS+3.6$\mu$M IBA

E. MS

?. Unknown condition

Figure 12:

FIG. 12 is a photograph showing the scanning electron micrograph of an ear culture showing the secondary ear formation. L, leaf; SP, spikelet; AX, axillary bud. Bar =50μX20.

Figure 13:

FIG. 13 is a photograph showing the Gynoecium formation in an in vitro developed ear culture on MS medium containing 500 mg/L CH and 1.0μM BA. X2.5.

Figure 14:

FIG. 14 is a photograph showing the development of fertile ears after in vitro pollination. The ears were cultured on MS medium containing 1.0μM BA and 1.8μM IBA. X0.6.

Figure 15:

FIG. 15 is a photograph showing the mature ear-bearing rooted plants in vitro. The leaves and husks covering the ears were removed to show the formation of kernels inside, X0.8

Figure 16:

FIG. 16 is a photograph showing a mature plant from in vitro produced seed. X0.06.

Figure 11:
FIG. 11 is a photograph showing the formation of several ears from a section of multiple shoot clump derived from seedling shoot tips five weeks after culture under light on MS medium containing 500 mg/L CH and 9.0μM BA. X10.
Figure 17:

FIG. 17 is a photograph showing anthesis in a terminal ear-bearing plant originally derived from multiple shoot forming ear cultures in FIG. 11. X0.2.

Figure 18:

FIG. 18 is a photograph showing a mature corn plant with a terminal ear. X0.2.

Figure 19:

FIG. 19 is a photograph showing multiple tassel formation from a section of multiple shoot clump derived from seedling shoot tips at the end of four subcultures at five week intervals on MS medium containing 500 mg/L CH and 9.0μM BA under dark. X 12.

GENERAL DESCRIPTION

The present invention relates to a method for sexual reproduction in corn plants, the improvement which comprises: growing immature ears or tassels of corn in a first growth medium containing a cytokinin alone or in admixture with an auxin and an amino acid source to provide an embryo; pollinating the embryo; and growing the pollinated embryo into a plant in the presence of an auxin.

The auxins which are particularly useful are 3,6-dichloro-o-anisic acid (dicamba); 2,4-dichlorophenoxyacetic acid (2,4-D); indole-3-acetic acid (IAA); indole-3-butyric acid (IBA); and α-naphthaleneacetic acid (NAA). The cytokinins are particularly 6-benzylaminopurine (or 6-benzyladenine) (BAP (or BA)); 6-furfurylaminopurine (Kinetin); and 6(4-hydroxy-3-methylbut-2-enylamino)purine (Zeatin).

The present invention particularly relates to a method for sexual reproduction in corn plants, the improvement which comprises: growing immature ears or tassels of corn in a first growth medium containing $N^6$-benzyladenine (BA) alone or in admixture with 2,4-dichlorophenoxy acetic acid and an amino acid source to provide an embryo; pollinating the embryo and growing the pollinated embryo into a plant in the presence of indole 3-butyric acid.

Further the present invention relates to a method for reproduction in corn plants which comprises: providing multiple immature ears of the corn plant from tassels, shoot tips or immature ears grown in a greenhouse; differentiating a portion of the immature ears in a first growth medium containing $N^6$-benzyladenine (BA) and an amino acid source to produce mature ovaries; pollinating the mature ovaries in a second growth medium containing indole 3-butyric acid (IBA) alone or in admixture with BA to produce kernels of the corn; and germinating the kernel to form the plant.

Further, the present invention relates to a method for in vitro sexual reproduction in corn plants which comprises: providing multiple shoot tips in a first growth medium containing $N^6$-benzyladenine (BA) and an amino acid source to produce multiple shoots; differentiating the shoot from the multiple shoots in a second growth medium containing BA and an amino acid source to produce multiple immature ears of the corn plant; differentiating a portion of the immature ears in a third growth medium containing BA and an amino acid source to produce mature ovaries; pollinating the mature ovaries in a fourth growth medium containing indole-3-butyric acid (IBA) alone or in admixture with BA to produce kernels of the corn; and germinating the kernel to form the plant.

The $N^6$-benzyladenine (BA) is preferably used in an amount between about 2.25 and 9 micrograms (μg) per liter of the medium to produce the shoot tips and to differentiate the shoot tips to produce immature ears The immature ears are preferably differentiated to ovaries in about 1.0 to 2.25μg of BA per liter of medium. Preferably between about 0.001 and 1.0μg per liter of medium of BA is used when pollinating mature ovaries. The BA need not be used in the pollinating step.

The amino acid source is preferably casein hnydrolysate (CH). The CH is used preferably in an amount between 0.5 and 1.0 grams per liter of medium.

The pollinating of the immature ovaries is in the presence of indole 3-butyric acid. This compound is used in an amount between about 1.8 and 3.6μg per liter of medium.

The in vitro morphogenetic pattern of corn (Zea mas L.) shoot tips excised from aseptically-grown seedlings, and of explants of axillary shoot buds, immature tassels an d ears (staminate and pistillate inflorescences) obtained from greenhouse grown corns was the basis for the present invention. The seedling shoot tips and immature ears first regenerated clumps of multiple shoots within four weeks of culture on Murashige and Skoog basal medium (MS) supplemented with 500 mg/L casein hydrolysate (CH) and 9.0μM $N^6$-benzyladenine (BA). Multiple shoot clumps were also differentiated from spikelets of immature tassels cultured on MS medium containing 500 mg/L CH, 4.5μM BA and 0.45μM 2,4-dichlorophenoxy acetic acid (2,4-D). All these multiple shoot clumps in turn differentiated clusters of ears after further four subcultures at four week intervals under light on MS medium supplemented with 500 mg/L CH and 2.25, 4.5, 9.0 or 18μM BA. Axillary shoot buds readily differentiated clusters of ears within four weeks of the initial culture on these media. Secondary and tertiary ear clusters were initiated following subculture of primary ears on MS medium containing 500 mg/L CH and 4.5 or 9.0 μM BA. Most of the ear primordia developed into ears with well developed ovaries and styles on subculture on MS medium containing 500 mg/L CH and 1.0μM BA. Corn kernels were obtained after pollination of in vitro formed ears with pollens collected from greenhouse grown corn. These kernels germinated in vitro and developed into mature corn plants in the greenhouse. Clusters of tassels were also differentiated in darkness from the multiple shoot clumps after six months successive subcultures but the spikelet primordia of tassels failed to develop fully under the in vitro conditions tested. Somatic embryos arose directly from spikelet primordia of young tassels of ears on MS medium containing 500 mg/L CH and 4.5μM 2,4-D, or indirectly from calli derived from spikelets of young tassels and ears on MS medium containing 500 mg/L CH and 9.0μM 2.4-D.

SPECIFIC DESCRIPTION

The shoot meristem can be experimentally manipulated to modify its normal pattern of morphogenesis by excising the meristem and culturing it in vitro. The shoot tips and immature ears and tassels can be interconverted to form multiple shoot clumps, ear and tassel clusters and somatic embryos under in vitro conditions.

MATERIALS AND METHODS

A. Culture of tassels and ears

To obtain explants for tassel and ear cultures, plants of sweet corn (ea mays L. cv. Honey N Pearl, HNP, Illinois Foundation Seeds, Inc., Champaign, IL., USA) were raised from seeds (caryopses, kernels) in 40 cm pots containing Baccto Pro. Plant. Mix (Michigan Peat Co., Houston, TX. USA), fertilizing weekly with Peters 20:20:20 fertilizer (W. R. Grace & Co., Cambridge, Mass., USA), in a temperature controlled greenhouse during the spring and summer seasons (800 $\mu E.m^{-2}.S^{-1}$, 16 h/d, 24°-30° C.).

Culture of immature tassels. When the plants unfurled five to seven leaves (45-60 days after planting the kernels), shoots were harvested and used to extract the tassels. After removing two or three outermost leaves, about 5 cm long cylinders of stem with leaf sheaths, enclosing the young tassels, were surface sterilized first in 70% ethanol for 10 minutes and washed once with sterile water; then, they were rinsed three times with autoclaved water after being soaked with 0.525% sodium hypochlorite (prepared from commercial bleach containing 5.25% sodium hypochlorite) for 20 minutes. Yound tassels (2-20 mm length) were excited from the stem-sheath cylinders under a stereomicrosopce in a sterile laminar-flow hood. The tassels were immediately cultured onto agar-solidified Murashige and Skoog (Murashige, T., and Skoog, F., Physiol. Plant. 15 473-497 (1962) basal medium (MS-M5519) containing:

| | | |
|---|---|---|
| Ammonium Nitrate | 1650.0 | |
| Boric Acid | 6.2 | |
| Calcium Chloride (Anhydrous)* | 332.2 | |
| Cobalt Chloride-6H$_2$O | 0.025 | |
| Cupric Sulfate-5H$_2$O | 0.025 | |
| Na$_2$-EDTA | 37.26 | |
| Ferrous Sulfate-7H$_2$O | 27.8 | |
| Magnesium Sulfate (Anhydrous)** | 180.7 | |
| Manganese Sulfate-H$_2$O*** | 16.9 | |
| Molybdic Acid (Sodium salt)-2H$_2$O | 0.25 | |
| Potassium Iodide | 0.83 | |
| Potassium Nitrate | 1900.0 | |
| Potassium Phosphate Monobasic | 170.0 | |
| Zinc Sulfate-7H$_2$O | 8.6 | |
| Glycine (free base) | 2.0 | |
| Myo-Inositol | 100.0 | |
| Nicotinic Acid (free acid) | 0.5 | |
| Pyridoxine HCl | 0.5 | |
| Thiamine-HCl | 0.1 | |
| Grams of powder to prepare 1 liter | 4.4 | |

*Original formula contains calcium chloride dihydrate at 440.0 mg/L.
**Original formula contains magnesium sulfate heptahydrate at 370.0 mg/L.
***Original formula contains manganese sulfate tetrahydrate at 22.30 mg/L.

supplemented with 500 mg/L casein hydrolysate (CH) and 4.5 or 9.0μM 2,4-dichlorophenoxy acetic acid (2,4-D) in Petri dishes (100 mm diameter, 15 mm deep) for somatic embryogenesis. The pH of the medium was adjusted to 5.8 with 0.1 N sodium hydroxide before autoclaving and solidified with 7g/L phytagar (Gibco Lab, Grand Island, NY., USA). The tassel cultures were incubated at 25°-27° C. in darkness and they were subcultured once after four weeks of initial culture. The somatic embryos formed in the tassel cultures were transferred to MS medium containing 500 mg/L CH and 2.25μM benzyladenine (BA) for plant development. To induce multiple shoot clumps, the immature tassels were cultured on MS medium supplemented with 500 mg/L CH, 0.45μM 2,4-D and 4.5μM BA.

Culture of immature ears. After the plants had produced eight to ten leaves (65-75 days after planting the kernels), the shoots were sampled for excising ears and axillary shoot tips. The ears, enclosed in bracts, were cut from the nodes after removing the subtending leaves. Following surface sterilization as described above, the bracts were aseptically removed and the ears (1-20 mm length) were cultured for four weeks on MS medium amended with 500 mg/L CH, 4.5 or 9.0μM BA at 25°-27° C. in continuous light (60μE. $m^{-2}S^{-1}$ from cool white 40W Econ-o-watt fluorescent lamp (Philips Westinghouse, USA)) for shoot and secondary-ear formation. Similarly, axillary shoot tips containing three to five leaf primordia were also excised from the surface-sterilized shoot cylinders and cultured on the same medium under the same conditions. For somatic embryogenesis the ear explants were cultured on MS medium containing 500 mg/L CH and 4.5 or 9.0μM 2,4-D and incubated at 25°-27° C. in darkness. The ear cultures were routinely subcultured at four week intervals on the same medium and maintained under the same culture environment.

The shoots produced from all cultures were grown in a Magenta GA7 vessel weekly with 20:20:20 fertilizer (W. R. Grace & Co., Cambridge, MA) (65 mm. 65 mm. 100 mm; Magenta Corp., Chicago, IL., USA) on MS medium containing 2.25μM BA and 1.8μM indole acid (IBA) under light and rooted on MS medium containing 3.6μM IBA. The rooted plantlets were transplanted into the greenhouse in a soil mixture composed of 1:1 (v/v) peat and perlite and fertilized.

B. Shoot-tio cultures

Mature seeds (caryopses, kernels) of sweet corn cultivar Honey N Pearl (HNP) were surface sterilized and germinated in vitro. The surface sterilization was with 70% ethanol for 10 minutes, washed once with hypodolmite (prepared from commercial bleach) containing 0.1% by weight Tween 20 (polyoxyethylene sorbitan monooleate). The surface sterilized seeds were washed three times with sterile water and germinated aseptically on Murashige and Skoog (1982) basal medium (MS) in Petri dishes (100 mm diameter, 15 mm deep in darkness at 24±1° C. Five days after germination, a 5mm long section of the seedling containing a shoot apex, with a piece of stem immediately below it, and leaf primordia was excised and used as explants. The shoot tip explants were laid horizontally and partly buried in MS medium supplemented with 500 mg/L CH and 2.25, 4.5, 9.0, or 18μM of BA. Three shoot tips were cultured in a Petri dish, each containing 20 ml medium containing 500 mg/L casein hydrolysate and 9μM BA and the cultures were incubated at 25-27 ° C. in darkness. The cultures were transferred four or five times to the same medium every four weeks.

All chemicals used in this research including MS medium were obtained from Sigma chemical Company, St. Louis, MO. USA.

The scanning electron micrographs were obtained by fixation in 3% glutaraldehyde, dehydrated in an ethanol series critical point dried and washed with gold. Scanning electron micrographs were obtained with a JEOL (Tokyo, Japan) "JSM31".

C. Pollen collection from greenhouse-grown corn plants

Mature anthers were collected using a forced from the greenhouse-grown plants just before anthesis and surface-sterilized with 70% ethanol for 5 minutes. To pollinate in vitro formed ears, anthers were squashed with sterile forceps to shed the pollens on the in vitro grown silks (stigmas).

RESULTS

Figure 1:
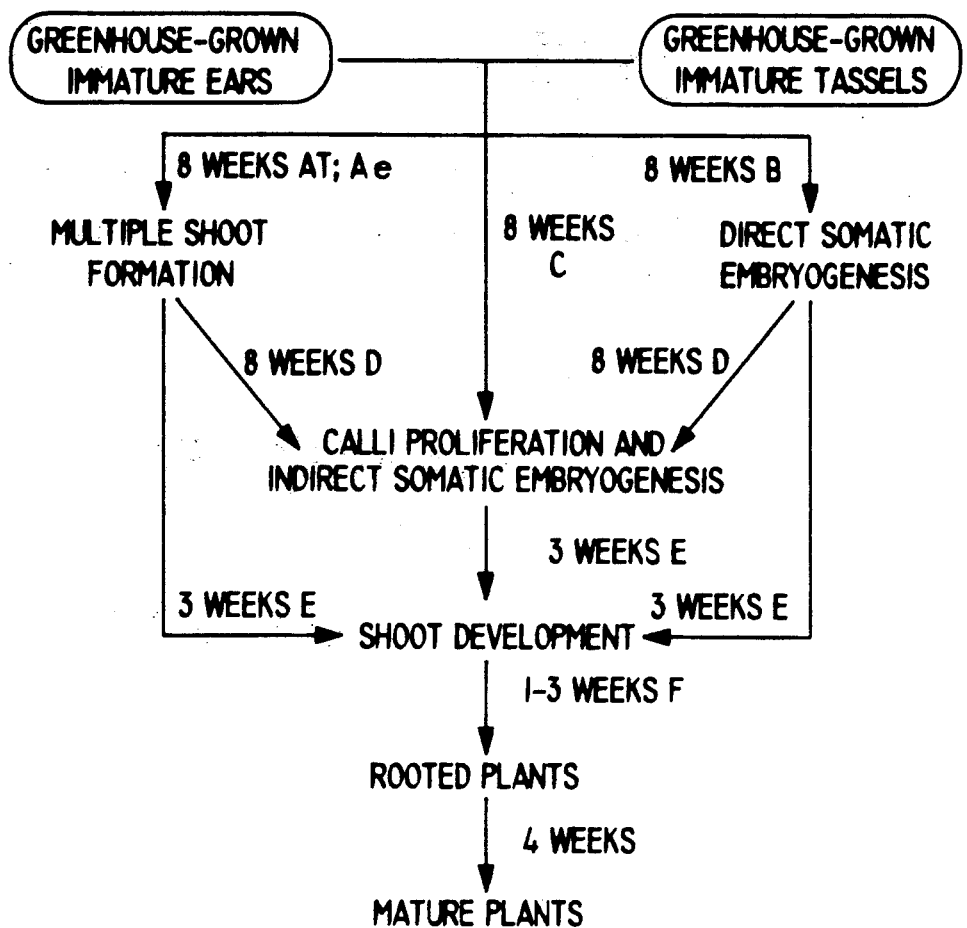
Figure 2:
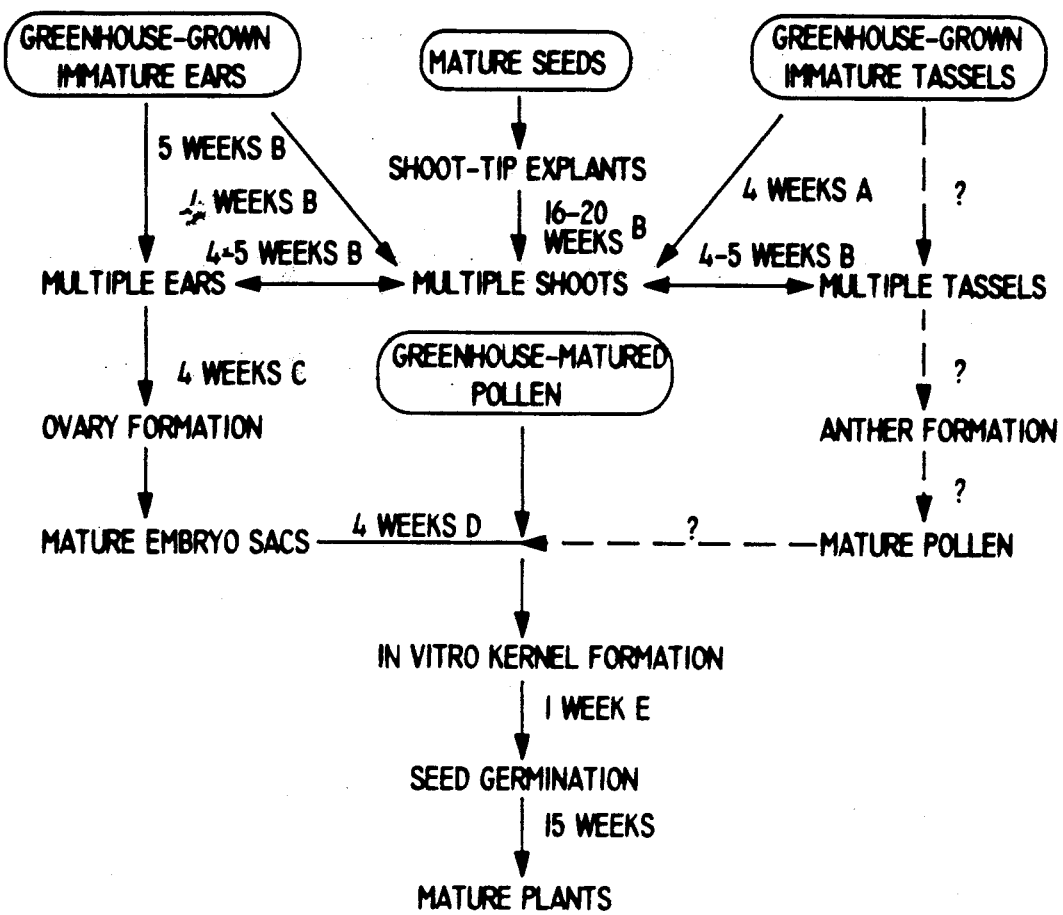

The various patterns of differentiation and interconversion of multiple shoot clumps, tassel and ear clusters in the cultures of seedling shoot tips, and immature tassels and ears are presented as flow diagrams in FIGS. 1 and 2.

Figure 3:
FIG. 3 is a photograph showing the germination of somatic embryos formed from an immature tassel culture on MS medium containing 500 mg/L CH and 2.25$\mu$M BA. X10.

Culture of immature tassels. Globular somatic embryos were formed from 2 to 5mm long tassel explants within four weeks of culture on 4.5$\mu$M 2,4-D under darkness. During this period the tassels enlarged three to five times and turned creamy white to pale yellow in color. The embryos appear to have originated directly from the spikelet primordia without apparent callusing. Following transfer of embryogenic-tassel cultures to the same medium, these globular embryos developed after another four weeks into mature somatic embryos. These embryos germinated on medium containing 500 mg/L CH and 2.25$\mu$M BA and developed into plantlets on 3.6$\mu$M IBA (FIG. 3).

Figure 4:
FIG. 4 is a photograph showing the adventitious shoot formation from a 3 mm long mature tassel culture on MS medium containing 500 mg/L CH, 0.45 $\mu$M 2,4-D and 4.5$\mu$M BA. X16.
Figure 5:
FIG. 5 is a photograph showing the shoot differentiation from male spikelets in a 7mm long tassel culture on MS medium containing 500 mg/L CH, 0.45$\mu$M 2,4-D and 4.5$\mu$M BA. XI6.
Figure 6:
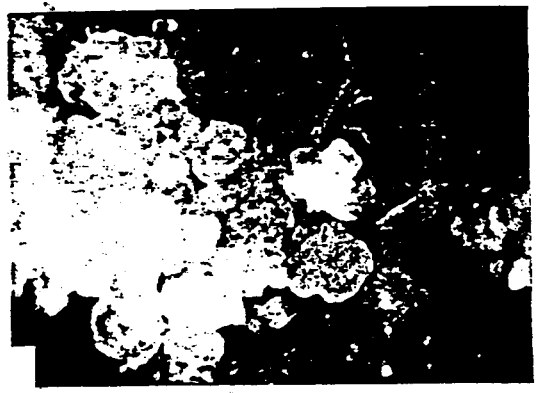
FIG. 6 is a photograph showing the callusing and somatic embryogenesis from a piece of 5mm long tassel on MS medium containing 500 mg/L CH and 9.0 $\mu$M 2,4-D. X20.

Tassels (2-5 mm long) which were cultured on MS medium containing 500 mg/L CH, 0.45$\mu$M 2,4-D and 4.5 $\mu$M BA, elongated and curved because of the preferential growth and development of the mid-section of the tassel explants. Most of the spikelets located in the middle region of the tassels differentiated into shoots without apparent callusing (FIGS. 4, 5). It is interesting that the orientation of the spikelets in the tassel in relation to the agar medium appears to alter their final response. Accordingly, those spikelets which were proximal to the agar medium, differentiated shoots while spikelets which happened to be distal to the medium atrophied. These spikelet-derived shoots produced groups of multiple shoot clumps. About 10 to 20 shoot tips were regenerated from each spikelet of a younger tassel (<5 mm long) within first three weeks (FIG. 4). These shoot clumps contained a mixture of both axillary and adventitious shoots. Spikelets of older tassels (5-10mm long) directly differentiated into shoots which later produced several axillary buds (FIG. 5). Shoot differentiation was very low or absent if the tassel explants were more than 10 mm long at the time of culture. These shoots have produced rooted corn plants similar to the somatic embryo-derived shoots. Tassel explants which were cultured on medium containing a relatively high 2,4-D (9.0$\mu$M) proliferated dense and nodular embryogenic calli within four weeks of culture. The calli differentiated embryos following further four weeks of subculture on 4.5$\mu$M 2,4-D (FIG. 6).

Figure 7:
FIG. 7 is a photograph showing the early stage of somatic embryogenesis from an immature ear explant one week after culture on MS medium containing 500 mg/L CH and 4.5$\mu$M 2,4-D. X16.
Figure 8:
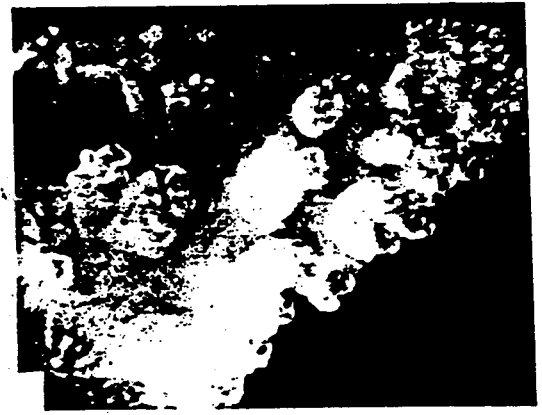
FIG. 8 is a photograph showing the direct shoot formation from spikelet primordia of a 5mm long ear explant on MS medium containing 500 mg/L CH and 9.0 $\mu$M BA. X20.
Figure 9:
FIG. 9 is a photograph showing the high frequency shoot formation from an immature ear culture after transfer to MS medium containing 2.25 $\mu$M BA and 1.8$\mu$M IBA. X0.6.

Culture of immature ears. The ear explants (about 5-10 mm long) differentiated translucent globular structures and developed into creamy white somatic embryos from the branch primordia with very little callusing on MS medium containing 500 mg/L CH and 4.5$\mu$M 2,4-D (FIG. 7). These somatic embryos matured and germinated on transfer to MS medium supplemented with 500 mg/L CH and 2.25$\mu$M BA. When the ears were cultured under light on MS medium supplemented with 500 mg/L CH and 9.0$\mu$M BA, the spikelets were converted into microscopic shoots within two to three weeks (FIG. 8). The frequency of shoot differentiation was less in relatively older (8 mm long) ear explants as compared to the younger (5 mm long) ones (FIG. 8). Most of spikelets in the younger ears differentiated into microscopic shoots. These shoots rapidly elongated and produced several axillary buds within four weeks. Transfer of these shoot-forming ear cultures to MS medium containing 2.25$\mu$M BA and 1.8$\mu$M IBA and on exposure to light resulted in the production of high frequency green shoot clumps (FIG. 9). In the presence of 9.0$\mu$M 2,4-D, the sections of immature ears (15 mm long) proliferated embryogenic calli in about three to four weeks. These calli have also organized into somatic embryos similar to the immature tassel cultures.

Figure 10:
FIG. 10 is a photograph showing the multiple ear formation from an axillary bud explant obtained from a greenhouse-grown corn plant four weeks after culture under light on MS medium containing 500 mg/L CH and 9.0 $\mu$M BA. X20.

Differentiation of multiple ears. Conical ear-like reproductive structures were observed on MS medium containing BA (2.25, 4.5, 9.0 or 18$\mu$M) and 500 mg/L CH under light in the cultures of axillary shoot buds (1-3 mm) excised from greenhouse-grown corn plants (FIG. 10). At early stages it was rather difficult to distinguish these undifferentiated structures as either tassels or ears. These reproductive structures were observed in all cultures regardless of the BA concentrations (2.25, 4.5, 9.0 or 18$\mu$M) in the medium, although the number of ear-like structures regenerated from each leaf axils of the axillary shoot bud was comparatively greater (five to ten) in cultures on MS medium containing 4.5 or 9.0$\mu$M BA than on the medium containing 2.25 or 18$\mu$M BA (one to six). When these ear-like structures were separated and individually cultured on 9.0$\mu$M BA, each primary structure in turn differentiated second and third order ears. After three successive transfers of ear-forming cultures to 9.0$\mu$M BA at four week intervals, the potential ear-forming meristem became shoots instead of ears.

Similar conical ear-like reproductive structures were also observed in seedling shoot tip cultures on BA-containing medium in darkness, at the end of four successive subcultures of four weeks each. During the first three transfers these shoot-tip cultures differentiated several supernumerary-miniature shoots in BA-containing media primarily because of the successive formation of second- and third-order axillary buds. About five weeks after the fourth transfer to BA-containing medium, shoot apices in the leaf axils of some of these miniature shoots elongated and produced long, white, columnar ear-like structures (FIG. 11).

Scanning electron microscope examination of ear forming cultures showed that the branch primordia and spikelet primordia in the primary ear appear to be converted into the secondary and tertiary ears (FIG. 12). Each spikelet was converted into a conical structure, each subtended by a overgrown bract. These structures later developed into compact shoots with terminal ears. Up to 12 ear shoots were produced from a shoot-tip culture within eight weeks of incubation. These ear-shoots rooted within two weeks of transfer to medium containing 1.0μM BA and 1.8μM IBA or 3.6μM IBA. The size of the ear also increased during rooting. On transplantation into potting soil in the greenhouse, the rooted ear shoots grew into dwarf corn plants with terminal ears (FIG. 18). In a few plants both ear and tassel were present in the same terminal inflorescence (FIG. 7). About 25 to 50 mature corn seeds were harvested from each plant.

Kernel formation and germination in vitro. The presumptive ears that were formed on 9.0μM BA developed miniature ears with several white globular ovaries with long styles (silks) within three to five weeks of transfer to a medium containing 500 mg/L CH and 1.0μM BA (FIG. 3. The rooted ear-forming shoots further grow to 5 to 10 mm length after being subcultured on 1.0 μM BA and 1.8μM IBA. Each of these mature ears bore 10 to 25 ovaries, each with one or two silks. The size of ovaries in an ear varied from 1 to 5 mm in diameter. When the silks were 6 cm long, twenty in vitro formed ears were hand-pollinated with pollens collected from greenhouse grown corn (FIG. 14). Kernel development was observed in 70% of the pollinated ears (FIG. 15). The ears matured in about three weeks after pollination. The number of kernels in each ear varied from one to eight but the size of all kernels was about 7 mm in diameter. Mature seeds were collected in a Petri dish and air-dried for 24 hours under sterile conditions. These in vitro formed kernels germinated in vitro and grew and matured normally on transplantation to a greenhouse (FIG. 16).

Tassel formation in vitro. In a few shoot cultures, clusters of tassels were formed from multiple shoot clumps after six subcultures in darkness on 4.5 or 9.0 μM BA, but these incipient tassels did not mature to form male spikelets in any of the BA-containing media whether in darkness or in light (FIG. 19).

As can be seen from the foregoing experiments, BA, a synthetic cytokinin, induced in the cultured corn meristem a cascade of developmental events to produce either multiple shoot clumps or ears depending on its concentration and the duration of exposure of the explants to BA-containing medium (FIGS. 1, 2). This confirms the preliminary observation of Bommineni and Greyson (Bommeneni, V. R., and Greyson, R. I., Am. J. Bot. 74 883-890(1987)) was that the stage of ear explant at the time of initiation of culture is a critical factor in its final morphogenesis in vitro.

Contrary to the reports of Polowick and Greyson (Polowick, P. L. Greyson, R. I., Plant Sci. Lett. 26 139-145 (1982); Polowick, p L., Greyson, R. I., Can. J. Bot. 62 830-838 (1984); and Polowick, P. L. and Greyson, R. I., Can. J. Bot. 63 2196-2199(1985)) that cytokinins (kinetin and BA) support male spikelet development in cultured tassels, BA failed to develop male spikelets in tassel cultures. This contradiction may be due to the differences in the developmental stage of the tassel at the time of culture initiation. Young tassel explants (2-5 mm long) differentiate into ears or shoots as observed in the present application, while comparatively older tassels (10 mm long) differentiate into male spikelets (Polowick, P. L., Greyson, R. I., Can J. Bot. 62 830-838 (1984)).

Corn plants bearing ear or both ear and tassel in the terminal position have been induced in vitro using BA (FIGS. 7, 8). This observation suggests that cytokinin appears to be involved in the conversion of tassels into ears in the terminal ear mutants report by earlier workers (Sheridan, W. F., Annu. Rev. Genet. 22 353-385 (1988)). Besides directing the spikelet meristems to form female flowers (FIG. 12), BA has also induced potentially floral spikelet meristems to form shoots (i.e. switch from reproductive to vegetative growth) (FIG. 8). Such dual morphogenetic role of BA was observed previously in Vitis vinifera L. where a relatively low concentration of BA has committed the meristem to form flowers while higher concentration of BA favored shoot formation.

Somatic embryos arose directly from the spikelet primordia without apparent callusing if young tassels and ears were cultured intact on a low (4.5 μM) 2,4-D medium. However, the intact inflorescences did produce embryogenic calli and then embryos when the 2,4-D concentration has been increased to 9.0μM. Embryogenic-callus formation precedes somatic embryogenesis even on low (4.5μM) 2,4-D if the ear and tassel explants were first sectioned before culture initiation (Rhodes, C. A., Green, C. E., and Phillips, R. L., Plant Sci. 46 225-232 (1986); and Pareddy, D. R., Petolino, J. F., Plant Sci. 67 211-219 (1990)).

The invention demonstrates that the corn meristem is morphogenetically plastic and it can be manipulated to produce somatic embryos, shoots, tassels or ears with fertile seeds under in vitro conditions by simple variation in culture conditions. These findings are important for studies of corn morphogenesis and for genetic improvement of corn using plant genetic engineering techniques.

It is important to note that transgenic plants are many times not fertile and produce no seed. Using the method of the present invention the immature meristem of the infertile transgenic plant could be used to produce the female part and then the female part could be pollinated. This is a very important result, since otherwise the transgenic plants are worthless.

It is intended that the foregoing description be only illustrative and that the present invention be limited only by the hereinafter appended claims.

We claim:

1. A method for in vitro sexual reproduction in a corn plant, the improvement which comprises:
   (a) growing multiple shoot tips derived from immature ears, tassels or shoot tips of corn in a growth medium containing a cytokinin alone or in admixture with an auxin and an amino acid source to provide an ovary from the multiple shoot tips, wherein the multiple shoot tips are grown to produce multiple ears such as shown in FIG. 10 which then multiple ears are grown to produce the ovary;
   (b) pollinating the ovary to produce an embryo; and
   (c) growing the pollinated embryo into the plant in the presence of an auxin.

2. A method for in vitro sexual reproduction in a corn plant the improvement which comprises:
   (a) growing multiple shoot tips from immature ears, tassels of corn or shoot tips in a growth medium containing N6-benzyladenine (BA) alone or in admixture with 2,4-dichlorophenoxy acetic acid and an amino acid source to provide an ovary from the multiple shoot tips, wherein multiple shoot tips are grown to produce multiple ears such as shown in FIG. 10 which then multiple ears are grown to produce the ovary;
   (b) pollinating the ovary to produce an embryo; and
   (c) growing the pollinated embryo into the plant in the presence of indole 3-butyric acid.

3. A method for in vitro sexual reproduction in a corn plant which comprises:
  (a) providing multiple immature ears of the corn plant such as shown in FIG. 10 from multiple shoot tips derived from shoot tips, immature ears or tassels grown in a greenhouse in a first growth medium containing $N^6$-benzyladenine to produce the immature ears;
  (b) differentiating a portion of the multiple immature ears in a second growth medium containing $N^6$-benzyladenine (BA) and an amino acid source to produce mature ovaries;
  (c) pollinating the mature ovaries in a third medium containing indole 3-butyric acid (IBA) alone or in admixture with BA to produce kernels of the corn; and
  (d) germinating the kernel to form the plant.

4. A method for in vitro sexual production in a corn plant which comprises:
  (a) providing shoot tips in a first growth medium containing $N^6$-benzyladenine (BA) and an amino acid source to produce multiple shoot tips wherein the multiple shoot tips are derived from shoot tips, tassels or immature rears grown in the first growth medium;
  (b) differentiating the multiple shoot tips in a second growth medium containing BA and an amino acid source to produce multiple immature ears of the corn plant such as shown in FIG. 10;
  (c) differentiating a portion of the immature eras, in a third growth medium containing BA and an amino acid source to produce mature ovaries; and
  (d) pollinating the mature ovaries in a fourth growth medium containing indole-3-butyric acid (IBA) alone or in admixture with BA to produce kernels of the corn; and
  (e) germinating the kernel to form the plant.

5. The method of claim 4 wherein the BA is present in an amount between about 2.25 and 9 $\mu$g per liter of BA in the medium in step (a), 2.25 and 9 $\mu$g per liter in the medium in step (b), and 1.0 to 2.25 $\mu$g per liter in the medium in step (c).

6. The method of claim 4 wherein the amino acid source in steps (a), (b) and (c) is casein hydrolysate (CH).

7. The method of claim 4 wherein the CH is used in an amount between about 0.5 and 10 g per liter of growth medium.

8. The method of claim 4 wherein the IBA is used in an amount between about 1.8 and 3.6 $\mu$g per liter of growth medium.

9. The method of claim 8 wherein the growth medium of step (d) contains BA in an amount between about 0.001 and 1.0 $\mu$g per liter of growth medium.

* * * * *

UNITED STATES PATENT AND TRADEMARK OFFICE
CERTIFICATE OF CORRECTION

PATENT NO. : 5,281,529
DATED : January 25, 1994
INVENTOR(S) : Heng Zhong and Masomeh B. Sticklen It is certified that error appears in the above-indentified patent and that said Letters Patent is hereby corrected as shown below:

Column 1, lines 29 and 30, open and closed parentheses --( )-- should be inserted before "Gengenback" and after (1977)".

Column 1, line 30, a period --.-- should be inserted after "(1977)".

Column 1, line 35, "basic" should be --basis--.

Column 2, line 9, "pieces" should be --apices--.

Column 2, line 17, before "MS", --B.-- should be inserted.

Column 4, line 27, "hnydrolysate" should be --hydrolysate--.

Column 5, line 17, "(ea" should read --(Zea--.

Column 5, line 37, "excited" should be --excised--.
Column 5, line 37, "Yound" should read --Young--.

Column 6, line 10, before "benzyladenine", --$N^{-6}$-- should be inserted.

Column 6, line 41, after "indole" and before "acid", -- -3-butyric-- should be inserted.

Column 6, line 47, "tio" should be --tip--.

UNITED STATES PATENT AND TRADEMARK OFFICE
CERTIFICATE OF CORRECTION

PATENT NO. : 5,281,529
DATED : January 25, 1994
INVENTOR(S) : Heng Zhong and Masomeh B. Sticklen It is certified that error appears in the above-indentified patent and that said Letters Patent is hereby corrected as shown below:

Column 9, line 65, "(FIGS. 7,8)." should read --(FIGS. 17, 18).--.

Column 11, line 25 (Claim 4), "rears" should be --ears--.

Column 12, line 3 (Claim 4), "eras" should be --ears--.

Column 7, line 14, "forced" should be --forcep--.

Column 9, line 14, "(FIG.3." should read --(FIG. 13).--.

Signed and Sealed this

Twenty-third Day of August, 1994

Attest:

BRUCE LEHMAN

Attesting Officer　　Commissioner of Patents and Trademarks